US007348000B2

(12) United States Patent
Dwek et al.

(10) Patent No.: US 7,348,000 B2
(45) Date of Patent: *Mar. 25, 2008

(54) THERAPEUTIC COMPOSITIONS AND METHODS OF TREATING GLYCOLIPID STORAGE RELATED DISORDERS

(75) Inventors: Raymond A. Dwek, Oxford (GB); Terence D. Butters, Oxford (GB); Mylvaganam Jeyakumar, Oxford (GB); Frances Mary Platt, Oxford (GB); David Priestman, Oxford (GB)

(73) Assignee: Actelion Pharmaceuticals Ltd, Allschwil (CH)

( * ) Notice: Subject to any disclaimer, the term of this patent is extended or adjusted under 35 U.S.C. 154(b) by 135 days.

This patent is subject to a terminal disclaimer.

(21) Appl. No.: 10/758,247

(22) Filed: Jan. 15, 2004

(65) Prior Publication Data
US 2005/0075305 A1  Apr. 7, 2005

Related U.S. Application Data

(63) Continuation of application No. 10/042,527, filed on Oct. 19, 2001, now abandoned, which is a continuation of application No. PCT/GB00/01560, filed on Apr. 20, 2000.

(30) Foreign Application Priority Data
Apr. 20, 1999 (GB) ................................ 9909066.4

(51) Int. Cl.
A61K 38/47 (2006.01)
A01N 43/40 (2006.01)
(52) U.S. Cl. .................................... 424/94.61; 514/328
(58) Field of Classification Search ...................... None
See application file for complete search history.

(56) References Cited

U.S. PATENT DOCUMENTS

| | | | |
|---|---|---|---|
| 4,182,767 A | 1/1980 | Murai et al. | |
| 4,266,025 A | 5/1981 | Kinast et al. | |
| 4,405,714 A | 9/1983 | Kinast et al. | |
| 5,151,519 A | 9/1992 | Behling et al. | |
| 5,580,884 A | 12/1996 | Platt et al. | |
| 5,786,368 A | 7/1998 | Platt et al. | |
| 6,291,657 B1 | 9/2001 | Platt et al. | |

FOREIGN PATENT DOCUMENTS

WO    WO 98/02161    1/1998

OTHER PUBLICATIONS

Ross G, Erickson R, Knorr D, Motulsky AG, Parkman R, Samulski J, Straus SE, Smith BR. Gene therapy in the United States: a five-year status report. Hum Gene Ther. Sep. 10, 1996;7(14):1781-90.*
Marshall E. Gene therapy's growing pains. Science. Aug. 25, 1995;269(5227):1050, 1052-5.*
Verma IM, Somia N. Gene therapy—promises, problems and prospects. Nature. Sep. 18, 1997;389(6648):239-42.*
Orkin SH and Motulski AG. Report and REcommendations of the Panel to Assess the NIH Investment in Research on Gene Therapy, Dec. 7, 1995.*
Rubanyi GM. The future of human gene therapy. Mol Aspects Med. Jun. 2001;22(3):113-42.*
Choo-Smith et al., Biol Chem, 272:22987-90 (1997).
Cox et al., The Lancet, 355:1481-1485 (2000).
Jeyakumar et al., Proc. Natl. Acad. Sci. USA, 96:6388-6393 (1999).
Meuilet et al., Experimental Cell Research, 256:74-85 (2000).
Overkleeft et al., J. Biol. Chem., 273:26522-26527 (1998).
Platt et al., Biochemical Pharmacology, 56:421-30 (1998).
Platt et al., J. Biol. Chem., 269:8362-6 (1994).
Platt et al., Science, 276:428-31 (1997).
Platt et al., J. Biol. Chem., 269:27108-27114 (1994).
Radin et al., *Glycoconj, J.*, 13:153-7 (1996).
Rosner et al., Ann N Y Acad Sci., 845:200-14 (1998).
Zervas et al., Current Biology, 11:1283-1287 (2001).
Beutler et al., Blood, 78:1183-1189 (1991).
Fredman et al., Glycoconjugate Journal, 13:391-399 (1996).
Glinsky et al., Cancer Research, 56:5319-5324 (1996).
Grabowski et al., Ann Intern Med., 122:33-39 (1995).
Yanagisawa et al., Nature Medicine, 1:1062-1067 (1995).
N. Asano et al., Tetrahedron: *Asymmetry*, 11:1645-1680 (2000).
D.A. Priestman et al., Glycobiology, 10:iv-vi (2000).
Gopalan et al., Kinetic analysis of the interaction of alkyl glycosides with two human β-glucosidases, Biochem J.,1989, 262:541-548.
Gatt et al., Use of activators and inhibitors to define the properties of the active site of normal and Gaucher disease lysosomal beta-glucosidase, Enzyme, 1985, 33(2):109-19, (Abstract Only).
Grabowski et al., Human Acid β-Glucosidase, The Journal of Biological Chemistry, 1986, 261:8263-8269.
Grace et al., Analyses of Catalytic Activity and Inhibitor Binding of Human Acid β-Glucosidase by Site-directed Mutagenesis, The Journal of Biological Chemistry, 1990, 265:6827-6835.
Warren et al., The effects of N-hexyl-O-glucosyl sphingosine on normal cultured human fibroblasts: a chemical model for Gaucher's disease, Journal of Lipid Research, 1976, 17:132-138.

(Continued)

Primary Examiner—Daniel M Sullivan
(74) Attorney, Agent, or Firm—Klauber & Jackson

(57) ABSTRACT

A method for treating a glycolipid storage-related disorder, comprising administering a therapeutically effective amount of an inhibitor of glycolipid synthesis in combination with an agent capable of increasing the rate of glycolipid degradation or in combination with bone marrow transplantation. Inhibitors of glycolipid synthesis include N-butyldeoxynojirimycin (NB-DNJ), N-butyldeoxygalactonojirimycin (NB-DGJ) or N-nonyldeoxynojirimycin (NN-DNJ). Glycolipid storage-related disorders include Gaucher disease, Sandhoff's disease, Fabry's disease, Tay-Sach's disease, Niemann-Pick C storage disease, GM1 gangliosidosis, genetic disorders in which neuronal glycolipid accumulation contributes to disease pathology.

6 Claims, 5 Drawing Sheets

OTHER PUBLICATIONS

Shafit-Zagardo et al., Human beta-glucosidase: inhibition by sulphates and purification by affinity chromatography on Dextran-sulphate-Sepharose, Biochim Biophys Acta, May 14, 1981, 659(1):7-14 (Abstract Only).

Blonder et al., Effects of detergents and choline-containing phospholids on human spleen glucocerebrosidase, Biochim Biophys Acta, Apr. 22, 1976, 431(1):45-53 (Abstract Only).

Saul et al., Castanospermine, a tetrahydroxylated alkaloid that inhibits beta-glucosidase and beta-glucocerebrosidase, Arch Biochem Biophys, Mar. 22, 1983, 221(2):593-7 (Abstract Only).

Sano et al., The inhibition of glucosylceramide β-glucosidase and other acid hydrolases by nucleic acids, Biochem J., 1988, 254:297-300.

Platt et al., Inhibitors of Glycosphingolipid Biosynthesis, Trends in Glycoscience and Glycotechnology, 1995, 7:495-511.

* cited by examiner

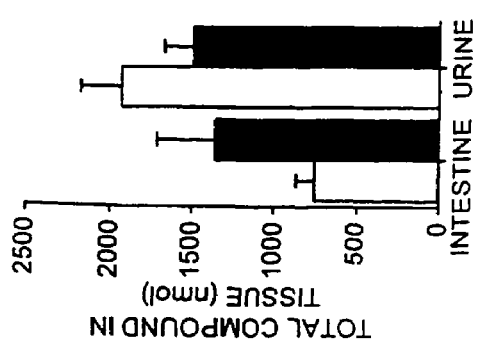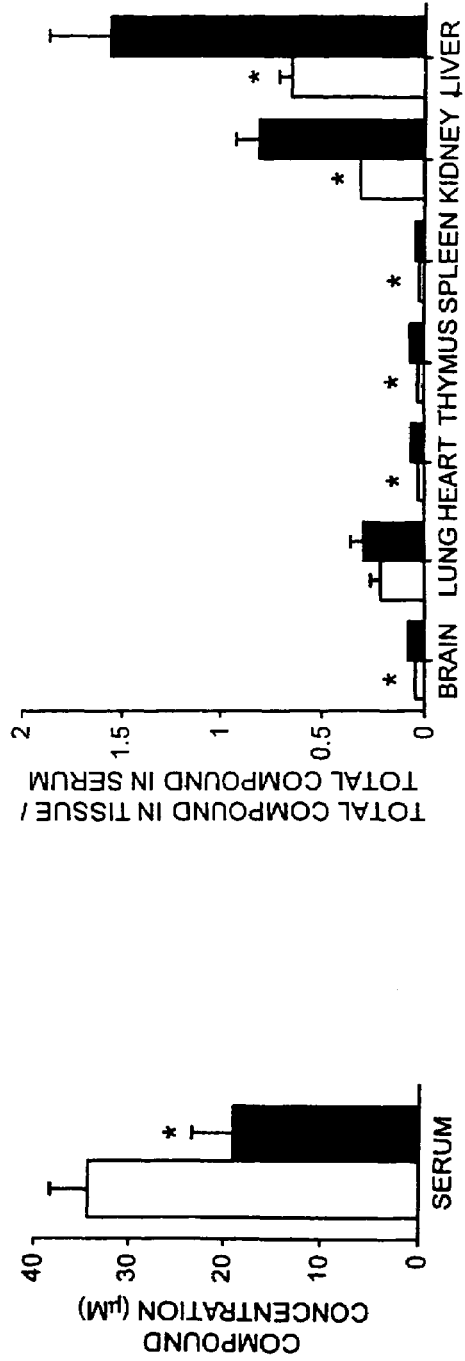

US 7,348,000 B2

THERAPEUTIC COMPOSITIONS AND METHODS OF TREATING GLYCOLIPID STORAGE RELATED DISORDERS

RELATED PATENT APPLICATIONS

This application is a continuation of application Ser. No. 10/042,527 filed Oct. 19, 2001, now abandoned, which is, in turn, a continuation of PCT/GB00/01560 filed Apr. 20, 2000, which in turn, claims priority from GB Application No. 9909066.4 filed Apr. 20, 1999. All of the afore noted applications are herein specifically incorporated by reference, and applicants claim the benefits of 35 U.S.C. § 120 as to said U.S. and PCT applications, and the benefits of 35 U.S.C. § 119 as to said GB application.

The present invention relates to compounds and methods of treatment of glycolipid storage related disorders, including such diseases as Niemann-Pick C storage disease, Gaucher disease, Sandhoff disease, Tay-Sach's disease, GM1 gangliosidosis, Alzheimer's disease, stroke, epilepsy and cancers such as glioblastoma and astrocytoma.

BACKGROUND OF THE INVENTION

The $G_{M2}$ gangliosidoses are a group of glycosphingolipid (GSL) lysosomal storage diseases which includes Tay-Sachs disease, Sandhoff disease and $G_{M2}$ activator deficiency (Gravel et al (1995) in The Metabolic and Molecular Bases of Inherited Disease (Scriver et al) Vol 2, pp 2839-79, 3 vols, McGraw Hill, New York). They result from mutations in the genes encoding the hexosaminidase α subunit, β subunit and $G_{M2}$ activator protein respectively. They are characterised by progressive neurodegeneration in response to high levels of lysosomal storage of $G_{M2}$ and related GSLs, in neurones of the central nervous system (CNS) (Gravel et al (1995) supra). There are currently no therapies for these diseases. Potential therapeutic strategies for Tay-Sachs and Sandhoff disease include enzyme augmentation and substrate deprivation (Radin (1996) Glycoconj. J 13:153-7; Platt et al (1998) Biochemical Pharmacology 56:421-30).

Enzyme augmentation could be achieved clinically through strategies such as enzyme replacement, bone marrow transplantation, or gene therapy.

Defects in ganglioside biosynthesis are found in most human cancers and are thought to underlie the invasive and malignant properties of brain tumours (Hakomori (1996) Cancer Res. 56:5309-5318, Fredman et al. (1996) Glycoconj. J. 13:391-399).

Glycolipid metabolism also plays a critical role in other neuronal disorders, such as Alzheimer's disease and epilepsy. Niemann-Pick Type C patient neurons present with fibrillar tangles reminiscent of the morphology seen in Alzheimer's disease. Interestingly, GM1 ganglioside binding by amyloid beta-protein induces conformational changes that support its formation of fibrous polymers, and the fibrillar deposition of this protein is an early event in Alzheimer's disease (Yanagisawa et al (1995) Nat Med 1:1062-6, Choo-Smith et al (1997) Biol Chem 272:22987-90). Thus, decreasing GM1 synthesis could inhibit the fibre formation seen in Alzheimer's disease.

The imino sugar N-butyldeoxynojirimycin (NB-DNJ) is a potent inhibitor of alpha-glucosidase 1 (involved in N-glycan synthesis), and an even more potent inhibitor of glucosylceramide glucosyltransferase. NB-DNJ is currently undergoing clinical trials as a treatment for Gaucher and Fabry diseases, glycolipid storage disorders resulting from mutations in glucocerebrosidase and alpha-galactosidase A, respectively.

SUMMARY OF THE INVENTION

The present invention is based, in part, on the discovery that NB-DNJ administered to mice together with glucocerebrosidase (the major therapy for Gaucher Type I patients) unexpectedly does not compromise the activity of glucocerebrosidase, and further, provides an augmentation of enzyme activity over time due to a protective effect of NB-DNJ on the enzyme. This result is surprising as the efficacy of the enzyme would be expected to be compromised in the presence of NB-DNJ, as NB-DNJ is a weak inhibitor of glucocerebrosidase ($IC_{50}$=0.52 mM). It has further been discovered that the co-administration of NB-DNJ with bone marrow transplantation to provide enzyme augmentation to increase the rate of neuronal glycolipid degradation provides an unexpected synergistic effect.

Accordingly, in one aspect, the invention features a method for treating a glycolipid storage-related disorder, comprising administering a therapeutically effective amount of an inhibitor of glycolipid synthesis in combination with an agent capable of increasing the rate of glycolipid degradation. In one embodiment, the inhibitor of glucosylceramide synthesis is an imido sugar. In more specific embodiments, the imido sugar is selected from the group consisting of N-butyldeoxynojirimycin (NB-DNJ), N-butyldeoxygalactonojirimycin (NB-DGN), and N-nonyldeoxynojirimycin (NN-DNJ). In specific embodiments, the inhibitor of glycolipid synthesis and the agent capable of increasing the rate of glycolipid degradation are given simultaneously, sequentially, or separately.

Disorders which result from accumulationl/storage of glucosylceramide-containing glycolipids include Gaucher disease, Sandhoff's disease, Fabry's disease, Tay-Sach's disease, Niemann-Pick C storage disease, GM1 gangliosidosis, genetic disorders in which neuronal glycolipid accumulation contributes to the disease pathology, e.g. mucopolysaccharidoses, neurological disorders in which glucosylceramide-containing glycolipid accumulation contributes to disease pathology such as Alzheimer's disease, stroke and epilepsy, cancers of neuronal origin such as glioblastoma and astrocytoma and cancers originating outside neuronal tissue but presenting with neuronal metastases.

In another embodiment of the method of the invention, the inhibitor is selected from the group consisting of 1-phenyl-2-decanoylamino-3-morpholino-1-propanol (PDMP), D-threo-1-phenyl-2-decanoylamino-3-morpholino-1-propanol or a structurally related analogue thereof.

In other embodiments of the method of the invention, the inhibitor is a nucleic acid encoding a peptide or protein capable of inhibiting glycolipid synthesis. In more specific embodiments, the nucleic acid is an antisense sequence, or a catalytic RNA capable of interfering with the expression of enzymes responsible for glycolipid synthesis.

In one embodiment of the method of the invention, the agent capable of increasing the rate of glycolipid degradation is an enzyme involved in glycolipid degradation. In more specific embodiments, the enzyme is selected from the group consisting of glucocerebrosidase, lysosomal hexoseaminidase, galactosidase, sialidase, and glucosylceramide glucosidase. In another embodiment, the agent capable of increasing the rate of neuronal glycolipid degradation is a molecule which increases the activity of a glycolipid degrading enzyme.

In further embodiments, the agent capable of increasing the rate of neuronal glycolipid degradation is a nucleic acid sequence which encodes a neuronal glycolipid degrading enzyme.

In a second aspect, the invention features a method for treating a glycolipid storage-related disorder, comprising administering a therapeutically effective amount of an inhibitor of glycolipid synthesis in combination with bone marrow transplantation. In one embodiment, the inhibitor of glucosylceramide synthesis is an imido sugar, and in more specific embodiments, the imido sugar is selected from the group consisting of N-butyldeoxynojirimycin (NB-DNJ), N-butyldeoxygalactonojirimycin (NB-DGN), and N-nonyldeoxynojirimycin (NN-DNJ). In a second embodiment, the inhibitor is selected from the group consisting of 1-phenyl-2-decanoylamino-3-morpholino-1-propanol (PDMP), D-threo-1-phenyl-2-decanoylamino-3-morpholino-1-propanol or a structurally related analogue thereof. In a third embodiment of this aspect of the invention, the inhibitor is a nucleic acid encoding a peptide or protein capable of inhibiting glycolipid synthesis, and may be an antisense sequence or a catalytic RNA capable of interfering with the expression of enzymes responsible for glycolipid synthesis.

In a third aspect, the present invention features a pharmaceutical composition useful for the treatment of glycolipid storage-related disorders, comprising a therapeutically effective amount of an inhibitor of glycolipid synthesis, an agent capable of increasing the rate of glycolipid degradation, and a pharmaceutically acceptable carrier. In one embodiment, the inhibitor of glucosylceramide synthesis is an imido sugar, and in more specific embodiments, the imido sugar is selected from the group consisting of N-butyldeoxynojirimycin (NB-DNJ), N-butyldeoxygalactonojirimycin (NB-DGN), and N-nonyldeoxynojirimycin (NN-DNJ). In a second embodiment, the inhibitor is selected from the group consisting of 1-phenyl-2-decanoylamino-3-morpholino-1-propanol (PDMP), D-threo-1-phenyl-2-decanoylamino-3-morpholino-1-propanol or a structurally related analogue thereof. In a third embodiment of this aspect of the invention, the inhibitor is a nucleic acid encoding a peptide or protein capable of inhibiting glycolipid synthesis, and may be an antisense sequence or a catalytic RNA capable of interfering with the expression of enzymes responsible for glycolipid synthesis.

In one embodiment of the pharmaceutical composition of the invention, the agent capable of increasing the rate of glycolipid degradation is an enzyme involved in glycolipid degradation. In more specific embodiments, the enzyme is selected from the group consisting of glucocerebrosidase, lysosomal hexoseaminidase, galactosidase, sialidase, and glucosylceramide glucosidase. In a further embodiment, the agent capable of increasing the rate of neuronal glycolipid degradation is a molecule which increases the activity of a glycolipid degrading enzyme. In a more specific embodiment, the agent capable of increasing the rate of neuronal glycolipid degradation is a nucleic acid sequence which encodes a neuronal glycolipid degrading enzyme.

BRIEF DESCRIPTION OF THE DRAWINGS

FIGS. 2-5 are graphs showing the short term distribution of radiolabelled NB-DNJ and NB-DGJ in mouse. Mice (n=5 per group) were dissected 90 min after oral administration of [$^{14}$C]-NB-DNJ (open bars) or [$^{3}$H]-NB-DGJ (filled bars). FIG. 2 total compound in intestine and urine. FIG. 3=total compound in organs. FIG. 4=compound concentration in serum. FIG. 5=compound in organs expressed as a ratio to compound in serum. * denotes a significant difference between the NB-DNJ and the NB-DGJ treated mice ($p<0.05$).

FIG. 6=$G_{M2}$ concentration in livers of mice fed 300-4800 mg/kg/day NB-DNJ (open bars) or NB-DGJ (filled bars) for 10 days, (n=5 per group). FIG. 7=TLC separated $G_{M2}$ band of livers from mice treated for 5 weeks with 2400 mg/kg/day. FIG. 8=densitometry of TLC in B. * denotes significantly lower concentration than the control concentration ($p<0.05$).

DETAILED DESCRIPTION OF THE INVENTION

Figure 1:
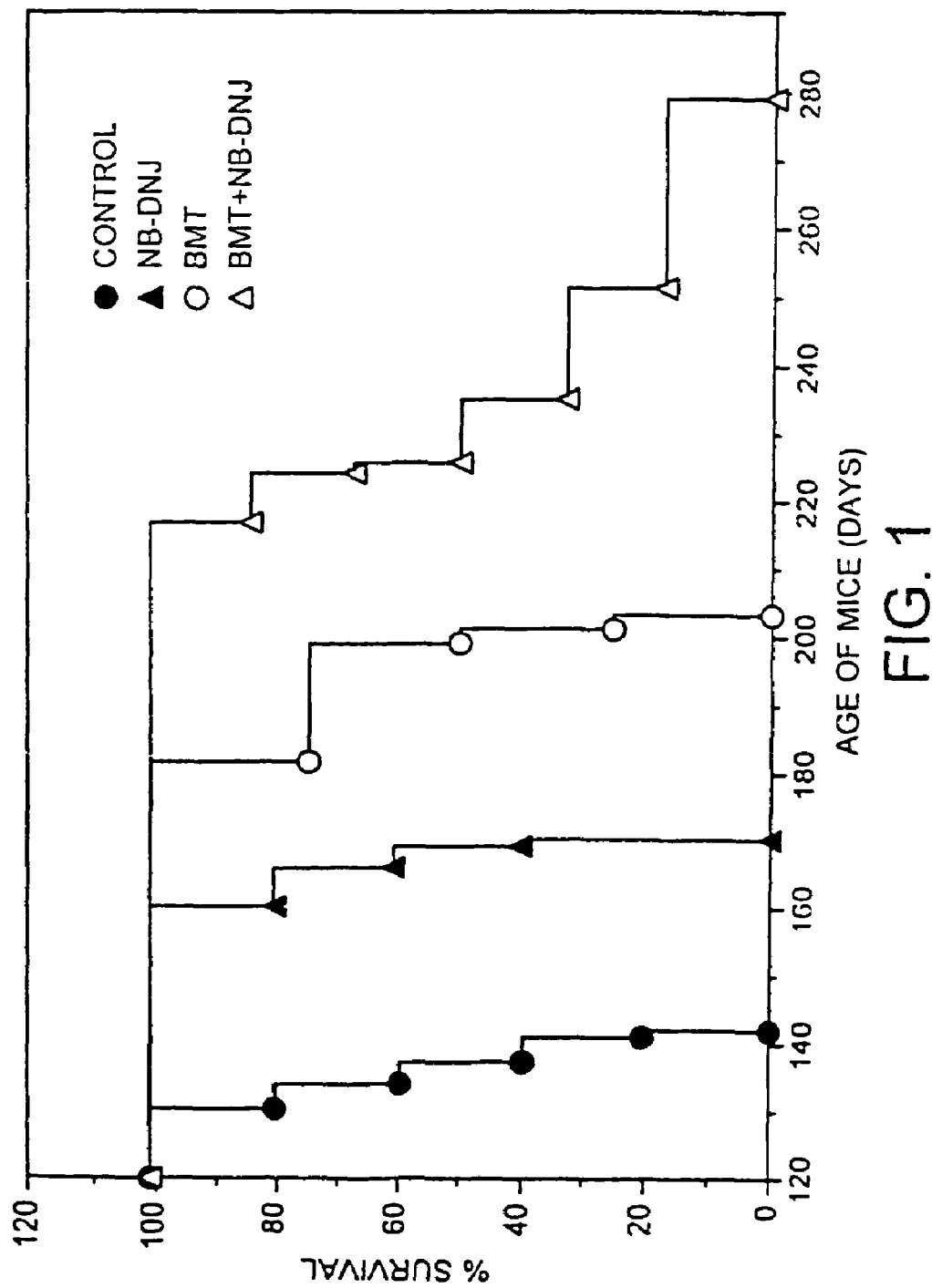
FIG. 1 is a graph plotting % survival against age of Sandhoff mice in days when treated with different agents.

Before the present methods and compositions are described, it is to be understood that this invention is not limited to particular methods, compositions, and experimental conditions described, as such methods and compounds may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "an inhibitor of glucosylceramide synthesis" includes mixtures of such inhibitors, reference to "the formulation" or "the method" includes one or more formulations, methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

DEFINITIONS

In the context of the present invention, the term "inhibitor" is intended to include inhibitors which inhibit glucosylceramide synthesis. It includes molecules such as N-butyldeoxynojirimycin, N-butyldeoxygalactonojrimycin, N-nonyldeoxynojirimycin and other imino sugar-structured inhibitors of glucosylceramide synthesis. It also includes other inhibitors of glycolipid synthesis, especially glucosylceramide synthesis, including agents such as 1-phenyl-2-decanoylamino-3-morpholino-1-propanol (PDMP), D-threo-1-phenyl-2-decanoylamino-3-morpholino-1-propanol and structurally related analogues thereof. Further, inhibition can also be achieved by the use of genetic approaches, based on the introduction of nucleic acid coding for proteins or peptides capable of inhibiting glycolipid synthesis or antisense sequences or catalytic RNA capable of interfering with the expression of enzymes responsible for glycolipid and especially glucosylceramide synthesis (e.g. glucosylceramide synthase). A combination of any of the above inhibitors can be used.

Furthermore, inhibition can also be achieved by the use of genetic approaches, based on the introduction of nucleic acid coding for proteins or peptides capable of inhibiting glucosylceramide synthesis or antisense sequences or catalytic RNA capable of interfering with the expression of enzymes responsible for glucosylceramide synthesis (e.g. glucosylceramide synthase). A combination of any of the above approaches can be used.

The term "substantially pure," when referring to a polypeptide, means a polypeptide that is at least 60%, by weight, free from the proteins and naturally-occurring organic molecules with which it is naturally associated. A substantially pure glucosylceramide synthesis inhibitor is at least 75%, more preferably at least 90%, and most preferably at least 99%, by weight, glucosylceramide synthesis inhibitor. A substantially pure glucosylceramide synthesis inhibitor such as N-butyldeoxynojirimycin (NB-DNJ), can be obtained, for example, by chemical synthesis or by isolation from natural sources. Purity can be measured by any appropriate method, e.g., column chromatography, polyacrylamide gel electrophoresis, or HPLC analysis.

"Treatment" refers to the administration of medicine or the performance of medical procedures with respect to a patient, for either prophylaxis (prevention) or to cure the infirmity or malady in the instance where the patient is afflicted.

A "therapeutically effective amount" is an amount of a reagent sufficient to achieve the desired treatment effect.

GENERAL ASPECTS OF THE INVENTION

Potential therapeutic strategies for disorders of diseases such as Tay-Sachs and Sandhoff diseases include enzyme replacement, bone marrow transplantation, or gene therapy. Intravenous administration of mannose-terminated glucocerebrosidase (β-D-glycosyl-N-acylsphingosine glucohydrolase, EC 3.2.1.45) is an effective therapy for type 1 Gaucher disease, which is a non-neurological GSL storage disease (Grabowski et al (1995) Ann. Intern. Med. 122:33-39; Beutler et al (1991) Blood 78:1183-9). However, as glycoprotein enzymes fail to cross the blood-brain barrier, this is not a suitable approach for disease involving GSL storage in the CNS. Bone marrow transplantation has the potential to increase enzyme levels in the periphery, and to a limited extent in the CNS due to secretion of enzyme from cells of bone marrow origin, including microglia (Krivit et al (1995) Cell-Transplant 4:385-392). Results of bone marrow transplantation in GSL lysosomal storage diseases involving storage in the CNS have been mixed (Hoogerbrugge et al (1995) Lancet 345:1398-1402). Partial success was recently reported in a mouse model of Sandhoff disease given syngeneic wild type bone marrow (Norfus et al (1998) J. Clin. Invest. 101:1881-8). This led to increased survival of the mice and improved neurological function. Gene therapy also has promise for treating these diseases, although this is currently experimental (Salvetti et al (1995) Br. Med. Bull 51: 106-122). Substrate deprivation is a potentially generic pharmacological approach for treating the GSL storage diseases (Platt et al (1998) Biochemical Pharmacology 56: 421-30), including the $G_{M2}$ gangliosidoses. This strategy is based upon partial inhibition of the ceramide specific glucosyltransferase (glucosylceramide synthase, UDP-glucose: N-acylsphingosine D-glucosyltransferase, EC 2.4.1.80) which catalyses the first step in GSL biosynthesis (Sandhoff et al (1998) Adv. Lipid Res. 26:119-142). This would reduce the levels of GSLs synthesised so they could be catabolised fully by the residual enzyme activity present in the cells.

Substrate deprivation, utilising the GSL biosynthesis inhibitor N-butyldeoxynojirimycin (NB-DNJ), has previously been tested in an in vitro model of Gaucher disease and shown to prevent storage (Platt et al (1994) J. Biol. Chem. 269:8362-6). NB-DNJ has also been evaluated in an asymptomatic mouse model of Tay-Sachs disease and shown to reduce $G_{M2}$ accumulation in the brain and prevent the neuropathology associated with its storage (Platt et al (1997) Science 276:428-31). NB-DNJ is currently under clinical evaluation in type 1 Gaucher disease.

The galactose analogue of NB-DNJ, N-butyldeoxygalactonojirimycin (NB-DGJ), is known to inhibit GSL synthesis in vitro as effectively as NB-DNJ, but is more specific in that it does not inhibit α-glucosidase I and II or β-glucocerebrosidase (Platt et al, (1994) J Biol Chem 269(43): 27108-14). It is known that only approximately 10% of the serum level of NB-DNJ is present in the cerebrospinal fluid. Accordingly, high systemic doses of NB-DNJ may have to be administered in order to achieve therapeutic levels in the CNS, and may have to be administered for the duration of a patient's life. High concentrations of NB-DNJ in humans causes diarrhoea and in mice it causes weight loss and reduces the size of lymphoid organs. Thus, it would be advantageous to have an inhibitor of glucosylceramide synthesis which does not have these disadvantages of NB-DNJ.

We have now shown that, when administered to healthy mice, the distribution of NB-DGJ in vivo is equivalent or superior to that of NB-DNJ and inhibited GSL synthesis. In addition and significantly, NB-DGJ does not appear to cause the side effects associated with NB-DNJ.

Thus, one specific embodiment, the invention provides a pharmaceutical composition of N-butyldeoxygalactonojirimycin and an agent capable of increasing the rate of glycolipid degradation for use in the treatment of a disorder which has at least a component based on glycolipid storage. The inhibitor of glycolipid synthesis and the agent capable of increasing the rate of glycolipid degradation may be provided as a combined preparation or separately for simultaneous, sequential or separate use in the treatment of a disorder which has at least a component based on glycolipid storage.

For example, it is envisaged that an inhibitor of glycolipid synthesis, such as NB-DNJ, can be administered to a patient with a glycolipid storage disease in order to maintain low levels of glycolipids. If the dosage of NB-DNJ is incorrect for any reason, an agent for increasing the rate of glycolipid degradation can be administered to restore the low levels of glycolipids.

Methods and processes for the production of N-butyldeoxynojirimycin can be found for example in U.S. Pat. Nos. 4,182,767; 4,266,025; 4,405,714; and 5,151,519; and in EPO B-0012278, and A-0624652.

Pharmaceutical Compositions and Methods of Administration

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In one specific embodiment, a non-human mammal is the subject. In another specific embodiment, a human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection by aerosol inhaler.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

The present invention also provides pharmaceutical compositions. Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric-acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of glycolipid storage related disorders can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Therapeutic Uses of Glucosylceramide Synthesis Inhibitors

The invention provides for treatment or prevention of glucosylceramide-containing glycolipid storage diseases and disorders, such as Gaucher disease, Sandhoff's disease, Fabry's disease, Tay-Sach's disease, Niemann-Pick C storage disease, GM1 gangliosidosis, and other genetic disorders, by administration of a therapeutic agent capable of inhibiting glycolipid synthesis and a glycolipid degrading enzyme or in combination with bone marrow transplantation. Agents capable of inhibiting glycolipid or glucosylceramide synthesis include but are not limited to: imide sugars such as N-butyldeoxynojirimycin, N-butyldeoxygalactonojirimycin, and N-nonyldeoxynojirimycin; compounds such as 1-phenyl-2-decanoylamino-3-morpholino-1-propanol (PDMP), D-threo-1-phenyl-2-decanoylamino-3-morpholino-1-propanol and structurally related analogues thereof; nucleic acids encoding a peptide or protein inhibitor of glucosylcermide synthesis; an antisense sequence or catalytic RNA capable of interfering with the expression of one or more enzymes required for glucosylceramide synthesis, such as, glucosylceramide synthase.

The change in glycolipid synthesis, in particular, gluyco-sylceramide synthesis, due to the administration of such compounds can be readily detected, e.g., by obtaining a biopsy sample, or by assaying in vitro the levels of activities of enzymes involved in glucosylceramide synthesis, or the levels of mRNAs encoding such enzymes, or any combination of the foregoing. Such assays can be performed before and after the administration of the compound as described herein.

In one embodiment, a nucleic acid comprising a sequence encoding a peptide or protein inhibitor of glucosylceramide synthesis is administered. In another embodiment, a nucleic acid sequence encoding an agent capable of increasing the rate of neuronal glycolipid degradation, e.g., a glucosylceramide glucosidase, is administered. Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspects, the compound comprises a nucleic acid encoding a peptide or protein inhibitor of glucosylceramide synthesis or encoding an enzyme required for neuronal glycolipid degradation, such nucleic acid being part of an expression vector that expresses a the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342: 435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432) which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342:435-438).

In a further embodiment, a viral vector that contains a nucleic acid encoding a glycolipid degrading enzyme is used, for example, a retroviral vector can be used (see Miller et al. (1993) Meth. Enzymol. 217:581-599). These retroviral vectors have been modified to delete retroviral sequences that are not necessary for packaging of the viral genome and integration into host cell DNA. The nucleic acid encoding the enzyme to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141, and Grossman and Wilson (1993) Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a preferred embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a preferred embodiment, the cell used for gene therapy is autologous to the subject that is treated.

In an embodiment in which recombinant cells are used in gene therapy, a nucleic acid encoding a peptide or protein inhibitor of glucosylceramide synthesis, or an agent capable of increasing the rate of neuronal glycolipid degradation is introduced into the cells such that it is expressible by the cells or their progeny, and the recombinant cells are then administered in vivo for therapeutic effect. In a specific embodiment, stem or progenitor cells are used. Any stem or progenitor cells which can be isolated and maintained in vitro can be used in accordance with this embodiment of the present invention (see e.g. PCT Publication WO 94/08598, dated Apr. 28, 1994; Stemple and Anderson (1992) Cell 71:973-985; Rheinwald (1980) Meth. Cell Bio. 21A:229; and Pittelkow and Scott (1986) Mayo Clinic Proc. 61:771).

In another embodiment, the nucleic acid to be introduced for purposes of gene therapy may comprise an inducible promoter operably linked to the coding region, such that expression of the nucleic acid is controllable by controlling the presence or absence of the appropriate inducer of transcription.

Direct injection of a DNA coding for a peptide or protein inhibitor of glucosylceramide synthesis or an agent capable of increasing the rate of neuronal glycolipid degradation may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection and the elicitation of an immune response in the subject to the protein encoded by the injected DNA.

In one embodiment of the invention, NPC is treated or prevented by administration of a compound that inhibits the expression of one or more enzymes responsible for glucosylceramide synthesis. Compounds useful for this purpose may include antibodies directed to glucosylceramide synthesis enzymes (and fragments and derivatives containing the binding region thereof), and antisense or ribozyme nucleic acids.

In a further embodiment, the expression of an enzyme involved in neuronal glucosylceramide synthesis is inhibited by use of antisense nucleic acids. The present invention provides the therapeutic or prophylactic use of nucleic acids comprising at least six nucleotides that are antisense to a gene or cDNA encoding an enzyme involved in glucosylceramide synthesis or a portion thereof. As used herein, an "antisense" nucleic acid refers to a nucleic acid capable of hybridizing by virtue of some sequence complementarity to a portion of an RNA (preferably mRNA) encoding an enzyme involved in glucosylceramide synthesis. The antisense nucleic acid may be complementary to a coding and/or noncoding region of an mRNA encoding an enzyme involved in glucosylceramide synthesis. Such antisense nucleic acids have utility as compounds that inhibit expression of an enzyme involved in glucosylceramide synthesis, and can be used in the treatment or prevention of neurological disorder.

The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The invention further provides pharmaceutical compositions comprising a therapeutically effective amount of an antisense nucleic acid which inhibits the expression of an enzyme involved in glucosylceramide synthesis, and a pharmaceutically-acceptable carrier, vehicle or diluent. The antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. The oligonucleotide can be modified at the base moiety, sugar moiety, or phosphate backbone. The oligonucleotide may include other appended groups such as peptides; agents that facilitate transport across the cell membrane (see, e.g., Letsinger et al. (1989) Proc. Natl. Acad. Sci. USA 86:6553-6556; Lemaitre et al. (1987) Proc. Natl. Acad. Sci. 84:648-652; PCT Publication No. WO 88/09810, published Dec. 15, 1988) or blood-brain barrier (see, e.g., PCT Publication No. WO 89/10134, published Apr. 25, 1988); hybridization-triggered cleavage agents (see, e.g., Krol et al. (1988) BioTechniques 6:958-976) or intercalating agents (see, e.g., Zon (1988) Pharm. Res. 5:539-549). In a particular aspect of the invention, a antisense oligonucleotide is provided, preferably of single-stranded DNA. The oligonucleotide may be modified at any position on its structure with substituents generally known in the art.

The antisense oligonucleotide may comprise any suitable of the following modified base moieties, e.g., 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, and other base analogs.

In another embodiment, the oligonucleotide comprises at least one modified sugar moiety, e.g., one of the following sugar moieties: arabinose, 2-fluoroarabinose, xylulose, and hexose.

In yet another embodiment, the oligonucleotide comprises at least one of the following modified phosphate backbones: a phosphorothioate, a phosphorodithioate, a phosphoramidothioate, a phosphoramidate, a phosphordiamidate, a methylphosphonate, an alkyl phosphotriester, a formacetal, or an analog of formacetal.

In yet another embodiment, the oligonucleotide is an, α-anomeric oligonucleotide. An, α-anomeric oligonucleotide forms specific double-stranded hybrids with complementary RNA in which, contrary to the usual, β-units, the strands run parallel to each other (Gautier et al. (1987) Nucl. Acids Res. 15:6625-6641).

The oligonucleotide may be conjugated to another molecule, e.g., a peptide, hybridization triggered cross-linking agent, transport agent, or hybridization-triggered cleavage agent.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, and methylphosphonate oligonucleotides can be prepared by use of controlled pore glass polymer supports (Sarin et al. (1988) Proc. Natl. Acad. Sci. USA 85:7448-7451).

In another embodiment, the antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Examples of such promoters are outlined above.

The antisense nucleic acids of the invention comprise a sequence complementary to at least a portion of an RNA transcript of a gene encoding an enzyme involved in glucosylceramide synthesis, preferably a human gene encoding an enzyme involved in glucosylceramide synthesis, however, absolute complementarity, although preferred, is not required. A sequence "complementary to at least a portion of an RNA," as referred to herein, means a sequence having sufficient complementarity to be able to hybridize under stringent conditions (e.g., highly stringent conditions comprising hybridization in 7% sodium dodecyl sulfate (SDS), 1 mM EDTA at 65° C. and washing in 0.1×SSC/0.1% SDS at 68° C., or moderately stringent conditions comprising washing in 0.2×SSC/0.1% SDS at 42° C. with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA encoding an enzyme involved in glucosylceramide synthesis it may contain and still form a stable duplex (or triplex, as the case may be). One skilled in the art can ascertain a tolerable degree of mismatch by use of standard procedures to determine the melting point of the hybridized complex.

Pharmaceutical compositions of the invention, comprising an effective amount of an antisense nucleic acid of the invention in a pharmaceutically acceptable carrier, vehicle or diluent can be administered to a subject having neurological disorder. The amount of antisense nucleic acid which will be effective in the treatment of a neurological disorder can be determined by standard clinical techniques.

In a specific embodiment, pharmaceutical compositions comprising one or more antisense nucleic acids to an enzyme involved in glucosylceramide synthesis are administered via liposomes, microparticles, or microcapsules. In various embodiments of the invention, such compositions may be used to achieve sustained release of the antisense nucleic acids.

Inhibitory Ribozyme and Triple Helix Approaches

In another embodiment, symptoms of a glycolipid storage-related disorder may be ameliorated by decreasing the level of an enzyme involved in glucosylceramide synthesis by using gene sequences encoding the an enzyme involved in glucosylceramide synthesis in conjunction with well-known gene "knock-out," ribozyme or triple helix methods to decrease gene expression of an enzyme involved in glucosylceramide synthesis. In this approach ribozyme or triple helix molecules are used to modulate the activity, expression or synthesis of the gene encoding the enzyme involved in glucosylceramide synthesis, and thus to ameliorate the symptoms of the disorder. Such molecules may be designed to reduce or inhibit expression of a mutant or non-mutant target gene. Techniques for the production and use of such molecules are well known to those of skill in the art.

Ribozyme molecules designed to catalytically cleave gene mRNA transcripts encoding an enzyme involved in glucosylceramide synthesis can be used to prevent translation of target gene mRNA and, therefore, expression of the gene product. (See, e.g., PCT International Publication WO90/11364, published Oct. 4, 1990; Sarver et al. (1990) Science 247:1222-1225).

Ribozymes are enzymatic RNA molecules capable of catalyzing the specific cleavage of RNA. (For a review, see Rossi (1994) Current Biology 4, 469-471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy mRNAs encoding an enzyme involved in glucosylceramide synthesis, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers (1995) Molecular Biology and Biotechnology: A Comprehensive Desk Reference, VCH Publishers, New York, (see especially FIG. 4, page 833) and in Haseloff and Gerlach (1988) Nature, 334, 585-591, each of which is incorporated herein by reference in its entirety.

Preferably the ribozyme is engineered so that the cleavage recognition site is located near the 5' end of the mRNA encoding the enzyme involved in glucosylceramide synthesis, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al. (1984) Science, 224, 574-578; Zaug and Cech (1986) Science, 231, 470-475; Zaug, et al. (1986) Nature, 324, 429-433; published International patent application No. WO 88/04300 by University Patents Inc.; Been and Cech (1986) Cell, 47, 207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the gene encoding the enzyme involved in glucosylceramide synthesis.

As in the antisense approach, the ribozymes can be composed of modified oligonucleotides (e.g., for improved stability, targeting, etc.) and should be delivered to cells that express the enzyme involved in glucosylceramide synthesis in vivo. A preferred method of delivery involves using a DNA construct "encoding" the ribozyme under the control of a strong constitutive pol III or pol II promoter, so that transfected cells will produce sufficient quantities of the ribozyme to destroy endogenous mRNA encoding the enzyme involved in glucosylceramide synthesis and inhibit translation. Because ribozymes, unlike antisense molecules, are catalytic, a lower intracellular concentration is required for efficacy.

Endogenous expression of an enzyme involved in glucosylceramide synthesis can also be reduced by inactivating or "knocking out" the gene encoding an enzyme involved in glucosylceramide synthesis, or the promoter of such a gene, using targeted homologous recombination (e.g., see Smithies et al. 1985) Nature 317:230-234; Thomas and Capecchi (1987) Cell 51:503-512; Thompson et al. (1989) Cell 5:313-321; and Zijistra et al. (1989) Nature 342:435-438, each of which is incorporated by reference herein in its entirety). For example, a mutant gene encoding a non-functional an enzyme involved in glucosylceramide synthesis (or a completely unrelated DNA sequence) flanked by DNA homologous to the endogenous gene (either the coding regions or regulatory regions of the gene encoding an enzyme involved in glucosylceramide synthesis) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene. However, this approach can be adapted for use in humans provided the recombinant DNA constructs are directly administered or targeted to the required site in vivo using appropriate viral vectors.

Alternatively, the endogenous expression of a gene encoding an enzyme involved in glucosylceramide synthesis can be reduced by targeting deoxyribonucleotide sequences complementary to the regulatory region of the gene (i.e., the gene promoter and/or enhancers) to form triple helical structures that prevent transcription of the gene encoding an enzyme involved in glucosylceramide synthesis in target cells in the body. (See generally, Helene (1991) Anticancer Drug Des. 6(6), 569-584; Helene et al. (1992) Ann. N.Y. Acad. Sci., 660, 27-36; and Maher (1992) Bioassays 14(12), 807-815).

Nucleic acid molecules to be used in triplex helix formation for the inhibition of transcription in the present invention should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In one embodiment, wherein the antisense, ribozyme, or triple helix molecules described herein are utilized to inhibit mutant gene expression, it is possible that the technique may so efficiently reduce or inhibit the transcription (triple helix) or translation (antisense, ribozyme) of mRNA produced by normal gene alleles of an enzyme involved in glucosylceramide synthesis that the situation may arise wherein the concentration of such an enzyme involved in glucosylceramide synthesis present may be lower than is necessary for a normal phenotype. In such cases, to ensure that substantially normal levels of activity of a gene encoding an enzyme involved in glucosylceramide synthesis are maintained, gene therapy may be used to introduce into cells nucleic acid molecules that encode and express an enzyme involved in glucosylceramide synthesis that exhibit normal gene activity and that do not contain sequences susceptible to whatever antisense, ribozyme, or triple helix treatments are being utilized. Alternatively, in instances whereby the gene encodes an extracellular protein, a normal enzyme can be co-administered in order to maintain the requisite level of activity.

Antisense RNA and DNA, ribozyme, and triple helix molecules of the invention may-be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Materials and Methods

Animals. Female C57BL/6 mice were housed under standard non-sterile conditions. The mice were provided with water ad libitum and prior to drug administration were fed pelleted chow (expended Rat and Mouse Chow 1, SDS Ltd., Witham, Essex, UK). All experiments were performed on age-matched animals.

Treatment of Mice with NB-DNJ and NB-DGJ. The mice (6 weeks old) were fed a diet of powdered chow (expended Rat and Mouse Chow 3, ground, SDS Ltd.) or diet containing NB-DNJ or NB-DGJ. The diet and compound (both as dry solids) were mixed thoroughly, stored at room temperature, and used within 7 days of mixing. The mice were maintained on NB-DNJ or NB-DGJ at doses of 300-4800 mg/kg/day for 10 days, or 2400 mg/kg/day for 5 weeks.

Radiolabelling of NB-DGJ. A galactose oxidase/Na[$^3$H]$_4$B method was used to radiolabel the C6-carbon of NB-DGJ. A solution of NB-DGJ (1.3 mg), galactose oxidase (80 units), and catalase (37000 units) in 200 μl 10 mM sodium phosphate buffer was incubated for 24 h at room temperature whilst stirring. The reaction was stopped by heating the solution to 95° C. for 5 min. After centrifuging (10 mins, 13000 rpm), 1M NaOH was added to the supernatant until pH 10-12 was achieved. Na[$^3$H]$_4$B (4.3 mCi) was added and the solution incubated for 2 h at 30° C., after which NaBD$_4$ (1 mg) was added and the solution incubated for 1 h at 30° C. The solution was neutralised with 1M acetic acid and then dried down. After removing borate by washing with acidified methanol (0.6% glacial acetic acid in methanol) 5-10 times, the [$^3$H]-NB-DGJ mixture was resuspended in water, added to an AG50-column (equilibrated with water) and eluted with 1-4 M NH$_3$. [$^3$H]-NB-DGJ was further purified on HPLC (Dionex CS10 hpcec chromatography, isocratic elution with 50 mM Na$_2$SO$_4$, 2.5 mM H$_2$SO$_4$, 2.5 mM H$_2$SO$_4$, and 5% ACN), and finally the AG50-column step was repeated.

Short-term Distribution of [$^{14}$C]-NB-DNJ and [$^3$H]-NB-DGJ in Mice. Mice were orally gavaged with 100 μl water containing 25 μg (106 cpm) [$^{14}$C]-NB-DNJ or [$^3$H]-NB-DGJ and 1 mg non-radiolabelled NB-DNJ or NB-DGJ, respectively. Urine and faeces were collected over 90 min. After 90 min the mice were killed and the serum, organs, and any additional urine and faeces were collected. Organs were homogenized in a four fold volume of water and faeces in a ten fold volume. Aliquots of 500 μl homogenate, 100 μl urine, or 50 μl serum were mixed with 4 ml scintillation fluid and [$^{14}$C] or [$^3$H] counts measured. The quenching by the different tissues of both isotopes was determined by measuring the counts of known amounts of radiolabelled compound added to tissue homogenates, and the results were corrected accordingly.

Glycosphingolipid Analysis of Mouse Liver. Liver samples were homogenised in water and lyophilised. Dried homogenates were extracted twice in chloroform:methanol (2:1, v/v), first overnight at 4° C. and then for 3 h at room temperature, pooled and dried under nitrogen. The extracts were resuspended in 500 μl chloroform:methanol (1:1, v/v), base-treated by adding 83 μl of 0.35 M NaOH in methanol and digested for 90 min at room temperature and partitioned by adding 83 μl water: methanol (9:1, v/v), 166.5 μl water and 416 μl chloroform. The upper phase containing the gangliosides was separated from the lower phase after mixing and low speed centrifugation, and the lower phase was washed twice with Folsh (chloroform:methanol:0.47% KCl, 3:48:47, v/v). Upper phases were combined, dried down to half volume under nitrogen, dialysed against water, lyophilised and resuspended in chloroform:methanol (2:1, v/v). An equivalent of 5 mg dry weight of tissue was separated by TLC chloroform:methanol: 0.22% CaCl$_2$, 60:35:8, v/v). The TLC plate was air-dried, sprayed with orcinol: sulphuric acid (0.2% (w/v): 2N), and heat-treated (90° C. for 10 min). The intensity of bands was quantified by scanning densitometry.

Determination of NB-DNJ and NB-DGJ Concentrations in Serum and Liver. Serum and supernatant of liver homogenate (130 mg/ml in 10% methanol) were centrifuged three times through a Millipore Ultrafree filter, after an internal standard (NB-pentylDNJ) had been added to the samples. The pooled filtrates were purified on an HCl preconditioned SCX column, eluted with 1% NH$_3$ in MeOH, dried down, resuspended in water, further purified on a C18 column (MeOH preconditioning, H$_2$O wash, and MeOH elution), and finally quantified by HPLC (Dionex CS10 hpcec chromatography, isocratic elution with 50 mM Na$_3$SO$_4$, 2.5 mM H$_3$SO$_4$, and 5% ACN).

Purification of Disaccharidases and Measurement of Sucrase, Maltase and Lactase Activity. The enzymes sucrase-isomaltase (EC 3.2.1.10/48) and lactase-phlorizin hydrolase (EC 3.2.1.62/108) were purified from porcine intestine at 4° C. as follows. The intestine (100 g) was cut into small pieces, washed by stirring in 250 ml of 150 mM NaCl/10 mM KCl for 30 min, and extracted twice with 125 ml of 2M urea, 50 mM EDTA, and 50 mM KCl at pH 7. The urea extracts were combined and homogenised (Waring blender), the homogenate was centrifuged at 60,000 g for 75 min, and the pellet was resuspended in 50 ml of a solution containing 10 mM EDTA and 10 mM L-cysteine-HCl in 50 mM potassium phosphate buffer at pH 7.5 (pre-equilibrated to 37° C.). After addition of papain (15 units/ml), the mixture was incubated for 30 min at 37° C., and centrifuged at 105000 g for 60 min. The supernatant was removed and precipitated in 75 ml of ethanol at −20° C. for 1 h. The precipitate was recovered by centrifugation at 5000 g for 10 min, dissolved in 5-10 ml of 10 mM potassium phosphate buffer at pH 7.5, and the solution was centrifuged at 30000 g for 60 min. The supernatant was removed and stored at 4° C. in the presence of 0.02% sodium azide. Sucrase, maltase and lactase activity were determined in the enzyme preparation (diluted to a suitable concentration) by incubating 50 μl enzyme. 125 μl sodium citrate buffer (60 mM, pH 6), and 125 μl disaccharide substrate at 37° C. for 30 min, heating to 100° C. for 3 min to inactivate the enzyme centrifuging the mixture at 13000 g for 10 min, and determining the glucose concentration by adding 50 μl of the supernatant to 1 ml trinder reagent (Sigma) and reading the absorbance at 505 nm after 18 min.

Statistical Analysis. Conventional statistical methods were employed to calculate mean values and standard errors of the mean (S.E.M.). Differences between groups of mice were tested for significance using Student's t-test for unpaired observations. Results in the text and tables are presented as means±S.E.M.

Example 2

Co-Administration of Ceredase™ and N-B-DNJ

A group of mice were treated with NB-DNJ at 4800 mg/kg/day for 5 weeks. After a low intravenous dose (5-10 U/kg) of Ceredase™ (Genzyme Corporation) administered as a single injection via the tail vein, serum enzyme activity was measured by taking sequential serum samples from the tail vein to monitor enzyme activity over time. Ceredase™ is a modified form of β glucocerebrosidase. The results are shown in Table 1.

TABLE 1

Effect of NB-DNJ on circulatory activity and half life of Ceredase ™

| Mouse | | Peak Activity | $T_{1/2}$ (min) |
|---|---|---|---|
| Control | 1 | 5.8 | 4.2 |
| | 2 | 7.9 | 3.3 |
| | 3 | 8.0 | 1.5 |

TABLE 1-continued

Effect of NB-DNJ on circulatory activity and half life of Ceredase™

| Mouse | | Peak Activity | $T_{1/2}$ (min) |
|---|---|---|---|
| | 4 | 6.8 | 1.8 |
| | 5 | 30.0 | 1.4 |
| | 6 | 2.8 | 2.0 |
| | 7 | 13.6 | 1.2 |
| | 8 | 17.6 | 1.2 |
| Mean ± sem | | 11.6 ± 3.1 | 2.1 ± 0.4 |
| NB-DNJ | 1 | 13.9 | 1.7 |
| | 2 | 32.1 | 4.9 |
| | 3 | 24.1 | 5.3 |
| | 4 | 13.1 | 3.0 |
| | 5 | 21.0 | 3.5 |
| | 6 | 68.3 | 2.4 |
| | 7 | 19.2 | 2.8 |
| Mean ± sem | | 27.4 ± 7.2 | 3.4 ± 0.5 |

Ceredase activity and serum half lives appeared to be increased in mice treated with NB-DNJ, suggesting a protective effect of the compound to enzyme clearance. It was concluded that (a) co-administration of NB-DNJ with Ceredase™ does not compromise activity and (b) there is a surprising augmentation of enzyme activity over time due to a protective effect of the compound on the enzyme.

Example 3

Co-administration of NB-DNJ and Bone marrow Transplantation in a Mouse Model of Sandhoff Disease Sandhoff mice were bone marrow transplanted at two weeks of age and drug therapy initiated at 9.5-11 weeks of age (600 mg/kg/day). Survival curves were plotted for each group of animals with each point on the graph representing a death (FIG. 1). The untreated (no BMT, no drug) survived (longest survivor) until 140 days (filled circles), NB-DNJ only (no BMT) survived until 170 days, BMT only (no NB-DNJ) survived until 200 days, and NB-DNJ plus BMT had extended survival from 200-280 days. The data show synergy approximately 13% above additive.

Example 4

Short-term Distribution of [$^3$H]-NB-DGJ and [$^{14}$C]-NB-DNJ in Mice

The short-term distribution of NB-DGJ and NB-DNJ in mice was determined by giving the compounds to mice by oral gavage, as described in Example 1. The radioactive counts in organs, serum, faeces and urine were measured after 90 min. The concentration of NB-DNJ was 28% higher than that of NB-DGJ in the total urine collected while in the intestine there was 77% more NB-DGJ than NB-DNJ (FIG. 2). This suggests that NVB-DGJ passed more slowly out of the gastrointestinal (GI) tract relative to NB-DNJ. There appeared to be no difference in distribution of the two compounds in other tissue (FIG. 3). The serum concentration however differed significantly with a lower level of NB-DGJ relative to NB-DNJ (FIG. 4), possibly reflecting the slower uptake of NB-DGJ from the GI tract. When adjusted for differential serum levels NB-DGJ was distributed to the tissue more efficiently than NB-DNJ (FIG. 5).

Example 5

Long Term Distribution of NB-DGJ and NB-DNJ in Mouse Serum and Liver

To assay the steady state levels of the compounds when administered long term via the oral route, the concentrations of NB-DGJ and NB-DNJ in serum and liver were determined by HPLC after treating mice with 2400 mg/kg/day of NB-DNJ or NB-DGJ (non-radiolabelled) for 5 weeks. The experiments were conducted as described in Example 1 above. The results are shown in Table 2.

Both serum and liver concentration of drug were higher in NB-DGJ treated mice compared to NB-DNJ treated (66±3.1 μM compared to 51±13.3 μM for serum, and 207±30.6 μM compared to 103±21.2 for liver). The level of NB-DGJ in liver compared to that of NB-DNJ suggests that NB-DGJ is selectively taken up into the liver as compared to NB-DNJ. Thus, NB-DGJ may enter tissues more efficiently and persist longer than NB-DNJ.

TABLE 2

Concentration of NB-DGJ and NB-DNJ in serum and liver: Mice were treated with 2400 mg/kg/day of NB-DGJ or NB-DNJ for 5 weeks (n = 2), and the compound concentration in serum and liver was then determined by duplicate runs on HPLC.

| | Compound concentration (μM) | |
|---|---|---|
| | Serum | Liver |
| NB-DGJ | 60 ± 3.1 | 207 ± 30.6 |
| NB-DNJ | 51 ± 13.3 | 103 ± 21.2 |

Example 6

Depletion of GSL by NB-DGJ and NB-DNJ

Figure 6:
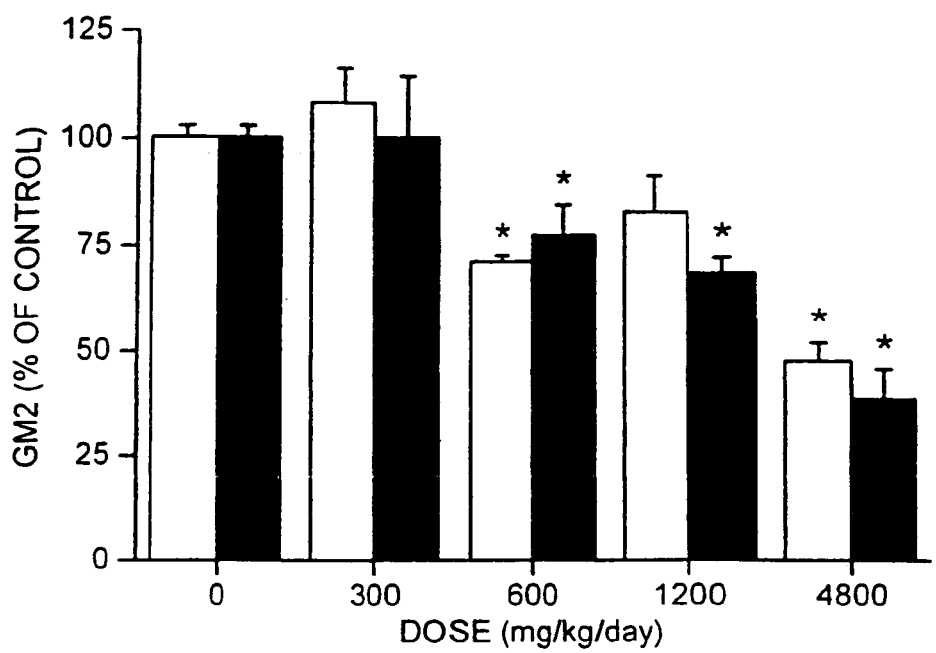
FIGS. 6-8 show glycosphingolipid depletion in mouse liver after feeding NB-DNJ or NB-DGJ. Gangliosides were purified from liver and separated by TLC. $G_{M2}$ concentration was measured by densitometry of the scanned TLC chromatograms.
Figure 7:
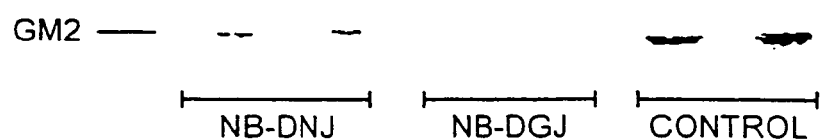
Figure 8:
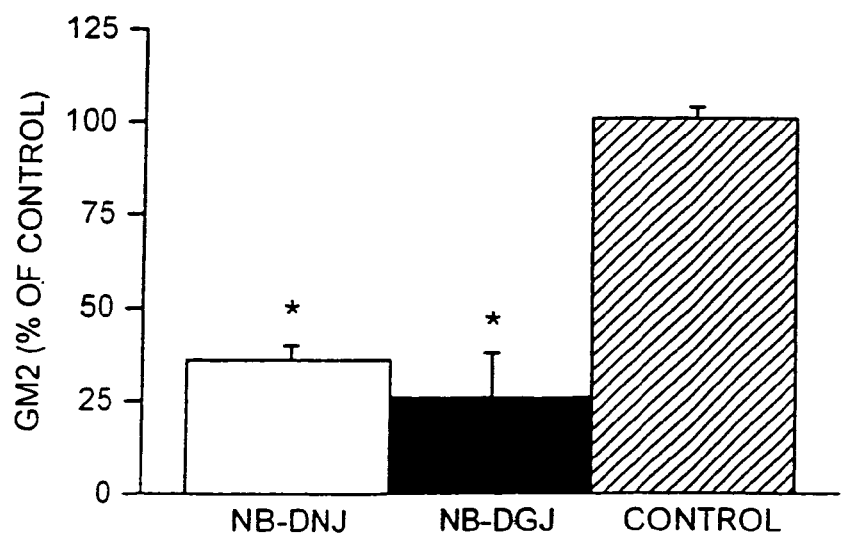

The degree of GSL depletion in liver after 10 days or 5 weeks of treatment was compared between mice administered NB-DGJ or NB-DNJ, using the methods described in Example 1. The livers were chloroform:methanol-extracted, gangliosides were analysed by thin layer chromatography and the $G_{M2}$ band intensity was quantitated by densitometry. The relative $G_{M2}$ concentrations (compared to control mice) in livers of mice treated with a range of NB-DGJ or NB-DNJ doses (300-4800 mg/kg/day) for 10 days show a dose-dependent response to both compounds (FIG. 6). There was no significant difference between the $G_{M2}$ depletion achieved by the two compounds at any of the concentrations tested. After longer treatment (2400 mg/kg/day for 5 weeks), the $G_{M2}$ concentrations in livers of mice treated with NB-DNJ or NB-DGJ were reduced to 35±4% and 26±11%, respectively, in relation to the concentration in control livers (FIGS. 7 and 8).

Thus, both analogues (NB-DNJ and NB-DGJ) were shown to be potent inhibitors of GSL biosynthesis in vivo. After 10 days of treatment, dose-dependent GSL depletion was seen in livers of mice fed either NB-DNJ or NB-DGJ. The lowest dose causing GSL depletion was 600 mg/kg/day (25% reduction). The highest dose evaluated (4800 mg/kg/day) caused 60-70% depletion. Similar data were obtained with both compounds. Although there is a two fold higher concentration of NB-DGJ in liver this was not observed when GSL depletion was measured, where both compounds gave comparable inhibition of $G_{M2}$ biosynthesis. This may reflect differential cellular uptake of the compounds into hepatocytes, endothelial cells and Kuppfer cells as $G_{M2}$ may be primarily the product of one cell type whereas the compound could be sequestered in non-$G_{M2}$ synthesising cells. GSL depletion after longer treatment at a dosage of 2400 mg/kg/day was also determined. After 5 weeks of feeding, the $G_{M2}$ concentration was reduced by 74% by NB-DGJ and 65% by NB-DNJ. The drug distribution and $G_{M2}$ depletion suggest treatment of GSL storage disorders should be as effective with NB-DGJ, since it has been shown that NB-DNJ reduces storage in mouse models of these diseases and NB-DGJ is slightly superior to NB-DNJ in inhibiting GSL biosynthesis in vivo.

Example 6

Effects of NB-DGJ and NB-DNJ on Growth and Lymphoid Organ Size

Figure 9:
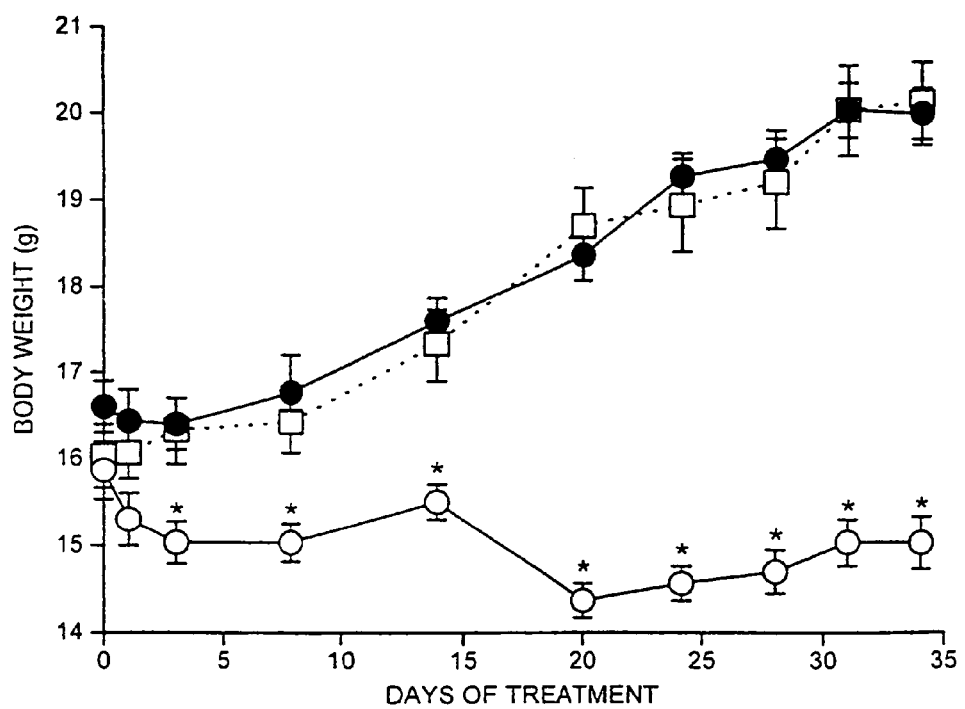
FIG. 9 shows the growth of mice fed NB-DNJ or NB-DGJ. Mice were given 2400 mg/kg/day of NB-DNJ (○), NB-DGJ (●), or a control diet (N=10 per group. * denotes a significant difference compared to control weights ($p<0.01$).
Figure 10:
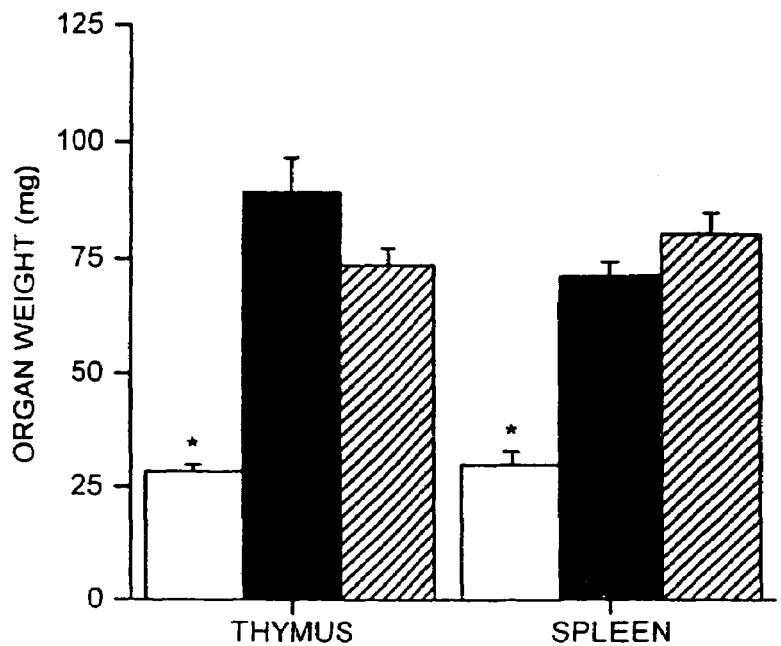
FIG. 10 shows the lymphoid organ size in mouse after NB-DNJ or NB-DGJ treatment. Wet weight of thymus and spleen was determined at dissection after 5 weeks of treatment with 2400 mg/kg/day of NB-DNJ (open bars). NB-DGJ (filled bars), or a control diet (dashed bars). N=4 per group. * denotes a significant difference compared to control weights ($p<0.001$).

To examine the overall well being of the mice treated with NB-DGJ or NB-DNJ (2400 mg/kg/day for 5 weeks) the mice were monitored 2-3 times per week, body weights recorded, and the effects of NB-DGJ and NB-DNJ on growth rates determined (FIG. 9). The NB-DNJ treated mice grew more slowly than untreated control mice, while NB-DGJ treated mice showed no difference in growth rates relative to the untreated controls. After 5 weeks of treatment, the NB-DNJ mice weighed 25% less than control and the NB-DGJ mice. Thymuses and spleens removed from NB-DNJ mice were smaller than those of control or NB-DGJ mice (FIG. 10), while the weights of other organs such as liver and kidney were unaffected. Treatment with NB-DNJ reduced the thymus weight by 61±2% and spleen weight by 62±3% compared to organs from control mice. In contrast, NB-DGJ had no effect on lymphoid organ weight. The loss of body weight in NB-DNJ mice did not account for the large reduction in lymphoid organ size. If expressed as a ratio to body weight, the organ weights were still reduced significantly (thymus to body weight ratio was reduced by 45±5% and spleen to body weight ratio by 48±4% in NB-DNJ mice compared to controls). It was observed that NB-DNJ treated mice had less fat associated with their organs (kidney, spleen etc.) and lacked subcutaneous fat compared to control or NB-DGJ treated mice (data not shown).

The fact that loss of body weight and reduction of lymphoid organ size is caused by NB-DNJ but not by NB-DGJ suggests that these effects are a function of glucosidase inhibition (or an as yet unidentified activity) by NB-DNJ, not GSL biosynthesis inhibition (an activity shared by both compounds). The effect of NB-DNJ in the present study on the inhibition of glycogen breakdown could provide a possible explanation for at least part of the weight loss observed in NB-DNJ treated mice. It was shown that, after 12 h of starvation, when the control and NB-DGJ treated mice had depleted most of their glycogen, NB-DNJ treated mice still had a significant amount of glycogen in their livers. Both following starvation and between episodes of feeding, the mouse would normally break down glycogen to provide the brain, muscles and other tissues of the body with glucose. However, if glycogenoloysis was partial inhibited, as in the NB-DNJ treated mice, the mouse would have to use other fuel sources, such as fat, to meet its energy demand. The store of adipose tissue would decrease with time resulting in reduced body weight. This hypothesis fits with the observation that the NB-DNJ treated mice (both fed and starved) had very little subcutaneous fat compared to normal or NB-DGJ treated mice. The inhibition of glycogenolysis by NB-DGJ is probably due to inhibition of the glycogen debranching enzyme (4-α-glucanotransferase, EC 2.4.1.25 and α-1,6-glucosidase, EC 3.2.1.33). Although never reported for NB-DNJ, inhibition of the α-1,6-glucosidase activity of this enzyme has previously been observed for other DNJ-derivatives (Arai et al. (1998) Circulation 97(13): 1290-7; Bollen et al. Eur-J-Biochem 181(3): 775-80). If this is also the case for NB-DNJ, over prolonged treatment periods this could cause (pathological) glycogen storage. If this does occur however, it is exceeding slow storage as animals on drug for prolonged periods in excess of six months show no overt signs of pathology (data not shown). What may be occurring is that the basal level of glycogen is increased due to partial enzyme inhibition, but that this remains relatively constant over time at the doses of inhibitor used in this study.

NB-DNJ treated mice had consistently smaller lymphoid organs. However, NB-DGJ did not show this effect, again implying that this is not the result of GSL biosynthesis inhibition in animals treated with NB-DNJ.

Example 6

Inhibition of Disaccharidases In Vitro

NB-DGJ, NB-DNJ and the parental non-alkylated compound DNJ were assessed for their capacities to inhibit the sucrase and maltase activities of the enzyme sucrase-isomaltase (which has disaccharidase activities for the breakdown of sucrose, maltose and isomaltose). Methods were as described in Example 1. Inhibition of this enzyme by DNJ has previously been reported (Hanozet et al. (1981) J. Biol. Chem 256:3703-3711). Both substrate and inhibitor concentrations were varied and the $K_i$ calculated (Table 3). NB-DNJ and DNJ were found to be potent inhibitors of both sucrase and maltase ($K_i$ (sucrase)=0.03 μM and $K_i$ (maltase)=0.07 μM for DNJ, and $K_i$ (sucrase)=0.26 μM and $K_i$ (maltase)=0.37 μM for NB-DNJ), while NB-DGJ was less potent ($K_i$ (sucrase)=2 mM, (maltase) non-inhibitor at 2 mM).

Figure 11:
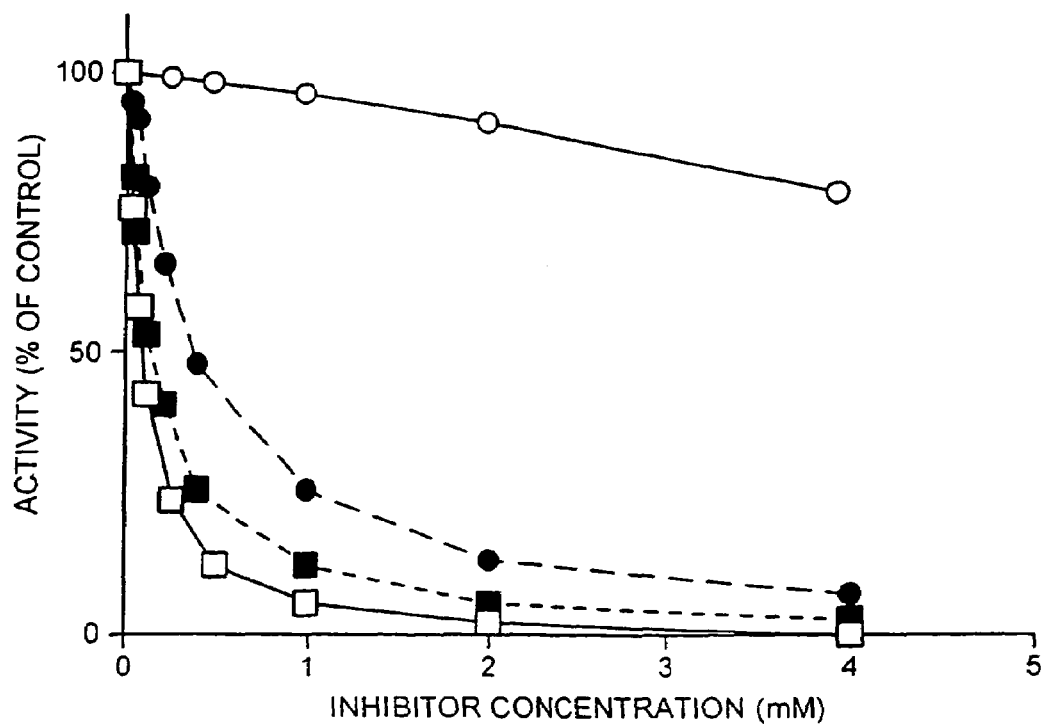
FIG. 11 shows the inhibition of lactase activity by NB-DNJ, NB-DGJ, DNJ, and DGJ. Lactase activity expressed as % of control activity at different concentrations of NB-DNJ (○), NB-DDJ (●), DNJ (and DGJ (■).

NB-DNJ, DNJ, NB-DGJ and DGJ were also tested for their capacity to inhibit lactase (FIG. 11 and Table 4). DNJ, NB-DGJ and DGJ all inhibited lactase ($K_i$ of 13 μM, 30 μM and 85 μM for DNJ, DGJ and NB-DGJ, respectively). Lactase inhibition by NB-DNJ was very weak ($K_i$=4 mM).

TABLE 3

$K_i$s for the inhibition of sucrase and maltase by DNJ, NB-DNJ and NB-DGJ.

| | $K_i$ (μM) | |
| --- | --- | --- |
| | Sucrase | Maltase |
| DNJ | 0.03 | 0.07 |
| NB-DNJ | 0.26 | 0.37 |
| NB-DGJ | 2000 | NI |

NI (non-inhibitory at 2 mM).

TABLE 4

$K_i$s for the inhibition of lactase by DNJ, NB-DNJ, DGJ and NB-DGJ.

| | $K_i$ (μM) |
| --- | --- |
| DNJ | 13 |
| NB-DNJ | 4000 |

TABLE 4-continued

K$_i$s for the inhibition of lactase by DNJ, NB-DNJ, DGJ and NB-DGJ.

| | K$_i$ (µM) |
|---|---|
| DGJ | 30 |
| NB-DGJ | 85 |

The primary side effect of NB-DNJ has been observed to be osmotic diarrhoea. The diarrhoea is thought to be caused by inhibition of disaccharidases in the intestine, which means that sugars like sucrose and maltose cannot be catabolised and absorbed from the digestive system. Sucrose consists of one glucose and one fructose residue, and maltose of two glucose residues. It is therefore not surprising that the results in this example show that the glucose analogues NB-DNJ and DNJ are very potent inhibitors of the sucrase and maltase activity while the galactose analogue NB-DGJ is not inhibitory. It was found that DNJ, NB-DGJ and DGJ all inhibited lactase, but the K$_i$s were at least $10^2$ times higher than for sucrase and maltase inhibition by the glucose analogues. NB-DNJ, however, was not a good inhibitor of lactase (K$_i$ 4 mM). In practical terms this means that NB-DGJ might be best tolerated on a lactose-free diet, but should not interfere with the digestion of other carbohydrates. The lack of side effects associated with NB-DGJ in vivo may have important implications for the potential treatment of infants and young children where these side effects could reduce tolerability to a greater extent than those experienced in adults.

Thus it can be seen that NB-DGJ has been shown to deplete GSL in vivo and to exhibit far fewer in vitro and in vivo enzyme inhibitory properties than NB-DNJ, making this a more selective compound. Of the activities listed below in Table 5, lactase inhibition is the only one associated with NB-DGJ and is probably the simplest to overcome by restricting dietary intake of lactose.

TABLE 5

| | NB-DNJ | NB-DGJ |
|---|---|---|
| GSL Biosynthesis | + | + |
| Weight loss | + | − |
| Lymphoid organ reduction | + | − |
| ER α-glucosidase I and II inhibition* | + | − |
| Sucrase and maltase inhibition** | + | − |
| Lactase inhibition*** | − | + |

*Platt et al (1994) J Biol Chem 269(43): 27108-14
**K$_1$ (sucrase) = 0.26 µM, K$_1$ (maltase) = 0.37 µM for NB-DNJ
***K$_1$ (lactase) = 85 µM for NB-DGJ
samples (shown in parentheses).

We claim:

1. A method for reducing accumulation of glucosylceramide-containing glycolipids in a patient afflicted with a glycolipid storage-related disorder, comprising administering to said patient afflicted with a glycolipid storage-related disorder an inhibitor of glycolipid synthesis in combination with an agent capable of increasing the rate of glycolipid degradation, wherein said inhibitor of glycolipid synthesis is N-butyldeoxynojirimycin (NB-DNJ) and is administered in an amount effective to reduce accumulation of glucosylceramide-containing glycolipids in said patient, and the agent capable of increasing the rate of glycolipid degradation is glucocerebrosidase.

2. The method of claim 1, wherein the glycolipid storage-related disorder is selected from the group consisting of Gaucher disease, Sandhoff's disease, Fabry's disease, Tay-Sach's disease, Niemann-Pick disease, GM1 gangliosidosis, Alzheimer's disease, stroke, and epilepsy.

3. The method of claim 1, wherein the inhibitor of glycolipid synthesis and the agent capable of increasing the rate of glycolipid degradation are given to said patient afflicted with a glycolipid storage-related disorder simultaneously, sequentially, or separately.

4. A method for augmenting glucocerebrosidase activity in a patient afflicted with a glycolipid storage-related disorder, comprising administering to said patient afflicted with a glycolipid storage-related disorder an inhibitor of glycolipid synthesis in combination with an agent capable of increasing the rate of glycolipid degradation, wherein the agent capable of increasing the rate of glycolipid degradation is glucocerebrosidase, and wherein said inhibitor of glycolipid synthesis is N-butyldeoxynojirimycin (NB-DNJ) and is administered in an amount effective to augment glucocerebrosidase activity in said patient.

5. A method for increasing the rate of glycolipid degradation in a patient afflicted with a glycolipid storage-related disorder, comprising administering to said patient afflicted with a glycolipid storage-related disorder an inhibitor of glycolipid synthesis in combination with an agent capable of increasing the rate of glycolipid degradation, wherein the agent capable of increasing the rate of glycolipid degradation is glucocerebrosidase and wherein the inhibitor of glycolipid synthesis is N-butyldeoxynojirimycin (NB-DNJ) and is administered in an amount effective to increase the rate of glycolipid degradation in said patient.

6. A method for improving survival of a patient afflicted with a glycolipid storage-related disorder, comprising administering to said patient afflicted with a glycolipid storage-related disorder an inhibitor of glycolipid synthesis in combination with an agent capable of increasing the rate of glycolipid degradation, wherein said inhibitor of glycolipid synthesis is N-butyldeoxynojirimycin (NB-DNJ) and is administered in an amount effective to improve survival of said patient, and the agent capable of increasing the rate of glycolipid degradation is glucocerebrosidase.

* * * * *